United States Patent [19]

Jegham et al.

[11] Patent Number: 5,280,030
[45] Date of Patent: Jan. 18, 1994

[54] PIPERIDINE DERIVATIVES, THEIR PREPARATION AND THEIR THERAPEUTIC APPLICATION

[75] Inventors: Samir Jegham, Franconville; Gérard DeFosse, Paris; Thomas Purcell, Montfort-l'Amaury; Johannes Schoemaker, Gif-sur-Yvettte, all of France

[73] Assignee: Synthélabo, Le Plessis-Robinson, France

[21] Appl. No.: 862,376

[22] Filed: Apr. 2, 1992

[30] Foreign Application Priority Data

Apr. 3, 1991 [FR] France .................. 91 04009

[51] Int. Cl.⁵ .................. C07D 401/14; A61K 31/445
[52] U.S. Cl. .................. 514/322; 514/318; 514/321; 546/193; 546/198; 546/199
[58] Field of Search .................. 546/198, 199, 193; 514/321, 322, 318

[56] References Cited

U.S. PATENT DOCUMENTS 4,634,704  1/1987  Jausseus .................. 546/194
4,879,301 11/1989  Umico .................. 546/198

FOREIGN PATENT DOCUMENTS 0197840 10/1986 European Pat. Off. .
0445026  9/1991 European Pat. Off. .

OTHER PUBLICATIONS

Tyers et al "5-HT₃ Receptors" N.Y. Academy Sci. 600 pp. 194–199, 215–216 (1990).
Foks et al "Pyraziue Derivatives" CA 90:168536m (1979).
Barchas et al "Serotonin and Behavior" Academic Press, pp. 235–238 (1973).
Glennon "Central Serotonin Receptors . . . " J. Med. Chem. 30(1) 1–12 (1986).

*Primary Examiner*—C. Warren Ivy
*Assistant Examiner*—Celia Chang
*Attorney, Agent, or Firm*—Wegner, Cantor, Mueller & Player

[57] ABSTRACT

A compound which is a piperidine derivative of general formula (I)

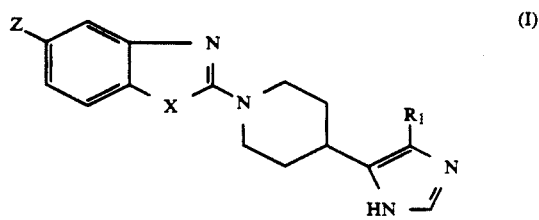

in which $R_1$ represents a hydrogen atom, a linear or branched $(C_{1-6})$alkyl group or a cyclo$(C_{3-8})$alkyl group, X represents an oxygen atom, a sulphur atom or a group of general formula N—$R_3$ in which $R_3$ is a hydrogen atom, or a linear or branched $(C_{1-8})$alkyl, cyclo$(C_{3-6})$alkyl, cyclo$(C_{3-6})$alkylmethyl, $(C_{1-4})$alkoxy-$(C_{1-4})$alkyl, phenyl, pyridin-4-yl, pyridin-3-yl, pyridin-4-ylmethyl or pyridin-3-ylmethyl group and Z represents a hydrogen or fluorine atom and acid addition salts thereof with pharmaceutically acceptable acids, can be used for the treatment and prevention of disorders in which 5-HT receptors are involved.

7 Claims, No Drawings

PIPERIDINE DERIVATIVES, THEIR PREPARATION AND THEIR THERAPEUTIC APPLICATION

The present invention relates to piperidine derivatives, their preparation and their therapeutic application.

SUMMARY OF INVENTION

The present invention provides a compound which is a piperidine derivative of general formula (I)

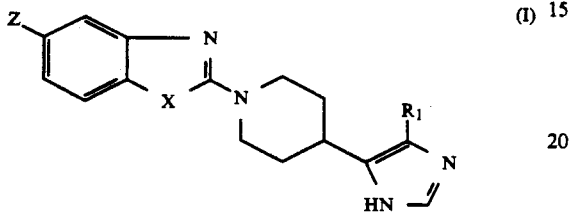

in which $R_1$ represents a hydrogen atom, a linear or branched ($C_{1-6}$)alkyl group or a cyclo($C_{3-8}$)alkyl group, X represents an oxygen atom, a sulphur atom or a group of general formula N-$R_3$ in which $R_3$ is a hydrogen atom, or a linear or branched ($C_{1-8}$)alkyl, cyclo($C_{3-6}$)alkyl, cyclo($C_{3-6}$)alkylmethyl, ($C_{1-4}$)alkoxy-($C_{1-4}$)alkyl, phenyl, pyridin-4-yl, pyridin-3-yl, pyridin-4-ylmethyl or pyridin-3-ylmethyl group and Z represents a hydrogen or fluorine atom and acid addition salts thereof with pharmaceutically acceptable acids.

The present invention also provides a process for the preparation of compounds of the invention.

DETAILED DESCRIPTION OF THE INVENTION

Preferred compounds of the present invention are compounds in which $R_1$ represents a hydrogen atom or a methyl or cyclohexyl group, X represents an oxygen atom, a sulphur atom or a group of general formula N—$R_3$ in which $R_3$ is a hydrogen atom, or a linear or branched ($C_{1-8}$)alkyl, cyclopropyl, cyclo($C_{3-6}$)alkylmethyl, methoxyethyl, phenyl, pyridin-4-ylmethyl or pyridin-3-ylmethyl group and Z represents a hydrogen or fluorine atom.

More preferred compounds according to the invention are the compounds in which $R_1$ represents a hydrogen atom or a linear or branched ($C_{1-6}$)alkyl group, X represents a group of general formula N—$R_3$ in which $R_3$ is a linear or branched ($C_{1-8}$)alkyl group, Z represents a hydrogen atom.

Finally, the preferred compounds are those in which $R_1$ represents with a hydrogen atom or a methyl group, X represents a (1-methylethyl)imino group, and Z represents a hydrogen atom.

The compounds of the invention may exist as free bases or addition salts with pharmaceutically acceptable acids. The compounds whose formula is a mesomeric form of the formula (I), form part of the invention.

Compounds according to the invention are prepared by reacting a compound of general formula (IX)

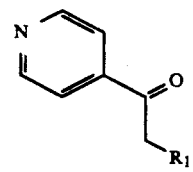

with hydroxylamine hydrochloride to obtain a compound of general formula (VIII)

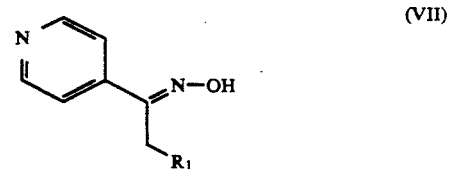

reacting the compound of general formula (VIII) with tosyl chloride to obtain a compound of general formula (VII)

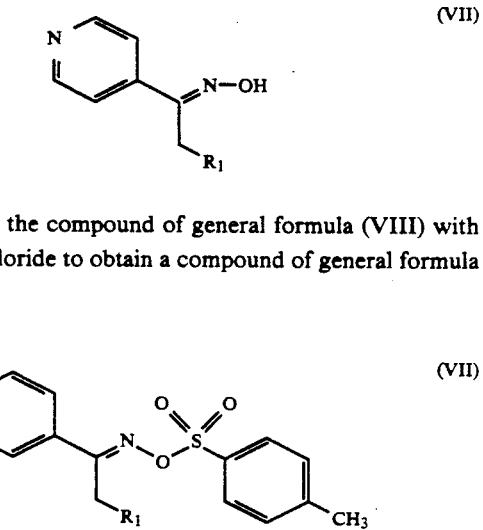

adding to the compound of general formula (VII) first a solution of potassium ethylate in absolute ethanol and then concentrated hydrochloric acid to obtain a compound of general formula (VI)

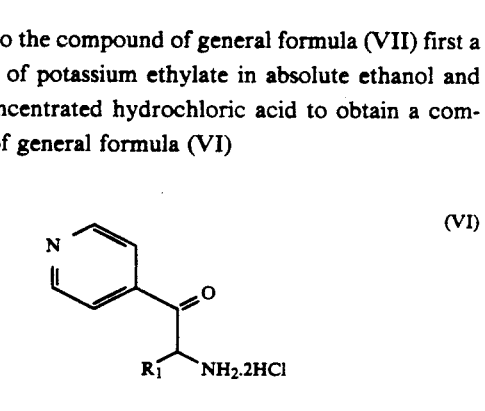

adding potassium thiocyanate to the compound of general formula (VI) to obtain a compound of general formula (V)

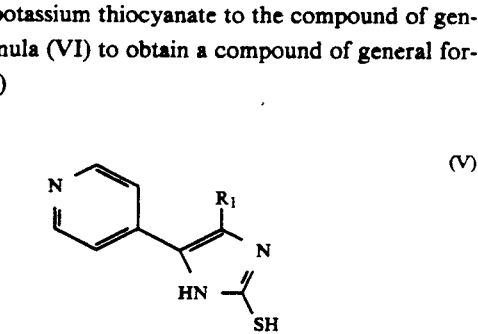

adding an oxidising solution to the compound of general formula (V) to obtain a compound of general formula (IV)

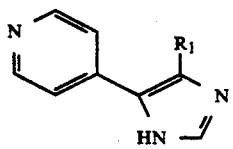

catalytically hydrogenating the compound of general formula (IV) to obtain a compound of general formula (III)

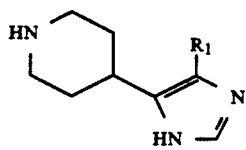

reacting the compound of general formula (III) with a compound of general formula (II)

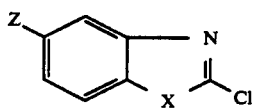

to produce a piperidine derivative of general formula (I) and, if desired converting the piperidine derivative of general formula (I) into an acid addition salt in a manner known per se, the symbols $R_1$, X and Z being as hereinbefore defined.

The reaction of the pyridine derivative of the general formula (IX) with hydroxylamine hydrochloride suitably takes place in the presence of concentrated sodium hydroxide in a solvent such as water. The compound of general formula (VIII) is reacted with tosyl chloride suitably in a solvent such as pyridine to obtain a compound of general formula (VII). This compound, after reaction with potassium ethylate in absolute ethanol, reacts so as to give an unstable cyclic intermediate which is hydrolysed, using concentrated hydrochloric acid suitably in water to obtain a compound of general formula (VI). The action of potassium thiocyanate on this compound leads to the formation of an imidazole ring carrying a mercapto group [compound (V)], which is removed by reacting with an oxidising solution such as for example an aqueous solution of nitric acid.

The process of the present invention is illustrated in the schematic representation in the appendix.

Suitable acid addition salts are the hydrochlorides, fumarates, maleates or oxalates.

The starting compounds are described in the literature or they may be prepared according to methods which are described therein or which are known to a person skilled in the art. The compounds of general formula (IX) in which $R_1$ represents a hydrogen atom are commercially available. Those for which $R_1$ is other than a hydrogen atom are prepared from 4-cyanopyridine by the action of the corresponding organomagnesium compound $R_1$-$CH_2$-Mg-Hal where Hal is Br or Cl, followed by acid hydrolysis. Chlorine-containing derivatives of general formula (II) in which X represents an oxygen atom are described in J. Med. Chem., 1988, 31, 1719–28. Those in whose formula X represents an N-phenyl group can be obtained from N-phenylbenzene-1,2-diamine, firstly by reaction with urea to form 1-phenylbenzimidazolone, and then by reaction with phosphoryl chloride.

The compounds of general formula (II), in which X represents an $NR_3$ group, and $R_3$ is as defined above, have been prepared using procedures similar to those described in J. Med. Chem., 1986, 29, 1178–83 and in European Patent No. 0,039,190.

4-(5-Methyl-1H-imidazol-4-yl)pyridine is described in J. Med. Chem., 1986, 29, 2154–63.

1-(Pyridin-4-yl)ethanone-oxime and 1-(pyridin-4-yl)ethanone-o-[(4-methylphenyl)sulphonyl]-oxime are described in Org. Synth., 1985, 64, 19–26.

4-(1H-imidazol-4-yl)piperidine is described in Arch. Pharmaz., (Weinheim. Ger.) 1973, 306(12), 934–42 and in European Patent Application 0,197,840.

Examples 1 to 2 below illustrate the preparation of some compounds of formula (II).

Examples 3 and 4 below illustrate in detail the preparation of compounds according to the invention.

Microanalyses and IR and NMR spectra confirm the structure of the compounds obtained.

EXAMPLE 1

2-Chloro-5-fluoro-1-(1-methylethyl)-1H-benzimidazole.

1.1. 4-Fluoro-N-(1-methylethyl)-2-nitrobenzenamine.

25 g (0.157 mole) of 2,5-difluoronitrobenzene and 40.3 ml (0.47 mole) of 1-methylethylamine are introduced into a round-bottom flask. The reaction is exothermic. The mixture is allowed to stand overnight. 500 ml of water are then added, the precipitate formed is drained, washed with water and dried under vacuum over phosphorus pentoxide. 31 g of compound are obtained.

Melting point: 48°–50° C.

1.2. 5-Fluoro-1(1methylethyl)-1H-benzimidazol-2(3H)-one.

31 g (0.156 mole) of the above compound dissolved in 200 ml of methanol and a catalytic amount of Raney nickel are introduced into a Parr apparatus. The hydrogenation is carried out for 1.5 hours at 50° C. at a pressure of 0.35 MPa. The nickel is then filtered. The colorless solution becomes brownish on contact with air. It is concentrated. 12.4 g (0.207 mole) of urea are added. The mixture is maintained at 180° C. for 3 hours. A solid magma is thereby obtained which is taken up in a small amount of hot water. The precipitate formed is drained and recrystallised from ethanol. 17 g of compound are obtained.

Melting point: 156° C.

1.3 2-Chloro-5-fluoro-1-(1-methylethyl)-1H-benzimidazole.

140 ml of phosphoryl chloride are added to 16 g (0.082 mole) of the above compound. This mixture is refluxed for 3 hours. The solvent is then evaporated, water is added and the mixture is made alkaline by means of sodium hydroxide. The mixture is then extracted with ether, dried and purified on a silica gel column, eluting with a mixture of ethyl acetate and hexane in proportions of 20/80 by volume. 12 g of pure compound are recovered.

Melting point: 60° C.

EXAMPLE 2

2-Chloro-1-(1-methylethyl)-1H-benzimidazole.

13.5 g (0.0885 mole) of 2-chloro-1H-benzimidazole, 9.2 ml of 1-bromo-1-methylethyl, 230 g of potassium carbonate and 200 ml of dimethyl sulphoxide are introduced into a round-bottom flask. The mixture is vigorously stirred for 4 hours while maintaining the temperature at 60° C. It is extracted several times with ether. The organic phases are combined and concentrated. The pasty residue is purified on a silica gel column eluting with a mixture of ethyl acetate and hexane in proportions of 20:80 v/v. The pure fractions are concentrated under vacuum. The residue is dissolved in 20 ml of hexane with the use of heat. The solution is cooled on a ice bath, the crystals are drained and then washed with a small amount of hexane and dried under vacuum. 12 g of compound are obtained.

Melting point: 62° C.

EXAMPLE 3

2-[4-(5-Methyl-1H-imidazol-4-yl)piperidin-1-yl]-1-(1-methylethyl)-1H-benzimidazole.

3.1. 1-(Pyridin-4-yl]propan-1-one oxime.

113 ml (1.13 moles) of 10 N sodium hydroxide are added to a solution of 79 g (1.13 moles) of hydroxylamine hydrochloride in 1 liter of water cooled on an ice bath, and 107 g (0.79 mole) of 1-(pyridin-4-yl)propan-1-one, prepared from 4-cyanopyridine according to the procedure described in Patent WO 85/02402, are then added over 5 minutes. 300 ml of methanol are added to this solution and the mixture is refluxed for 2 hours. The solution is cooled and forms a precipitate. The precipitate is drained and then dried under vacuum over phosphorus pentoxide. 96 g of compound are obtained.

Melting point: 152° C.

3.2. 1-(Pyridin-4-yl)propan-1-one-o-[(4-methylphenyl)-sulphonyl]oxime.

96 g (0.65 mole) of the above compound are added to a solution of 142 g (0.75 mole) of tosyl chloride in 500 ml of pyridine. The mixture is stirred for 24 hours and then the solution is poured on ice-cold water, the precipitate formed is drained, washed with water and then dried and recrystallised from 300 ml of isopropyl alcohol. 120 g of compound are obtained.

Melting point: 90° C.

3.3 2-Amino-1-(pyridin-4-yl)propan-1-one hydrochloride (2:1).

28 g (0.32 mole) of potassium ethylate in 250 ml of absolute ethanol are placed in a 2-liter reactor under an argon atmosphere. This solution is cooled by means of an ice bath and then a lukewarm solution of 79 g (0.26 mole) of the above compound in 400 ml of ethanol are added thereto. The mixture is stirred for 3 hours at room temperature, 1 liter of ether is then added and the potassium tosylate precipitate is filtered. The remaining organic solution is slowly poured, under an argon atmosphere, on 400 ml (0.8 mole) of 2 N hydrochloric acid. The mixture is decanted and the organic phase is washed with 100 ml of 2 N hydrochloric acid. The aqueous phases are then combined and concentrated under vacuum at a temperature of not more than 40° C. The residue is taken up in an ethanol/toluene mixture in proportions of 50:50 v/v. The resulting suspension is evaporated under vacuum to remove traces of water. The crystallised residue is taken up in 50 ml of hot ethanol. This solution is cooled, filtered, washed with ethanol and then dried under vacuum over phosphorus pentoxide. 49 g of compound are obtained.

Melting point: 210° C.

3.4 4-(2-Mercapto-5-methyl-1H-imidazol-4-yl)pyridine. 25.6 g (0.26 mole) of potassium thiocyanate are added to a solution of 49.7 g (0.22 mole) of the above compound in 210 ml of water, and the mixture is then heated at 100° C. for 1 hour by means of an oil bath. The solution is then cooled to 30° C., the precipitate is filtered, washed with water and then dried and added, without stirring, to a solution of sodium bicarbonate. The precipitate is drained, washed with water and dried. 33 g of compound are obtained.

Melting point: >290° C.

3.5. 4-(5-Methyl-1H-imidazol-4-yl)pyridine.

33 g (0.172 mole) of the above compound are placed in a 6-liter reactor in the presence of 255 ml of nitric acid (d=1.41) and 1.4 liters of water. The mixture is heated to 85° C. with stirring and the oxidation reaction occurs violently with the release of sulphurous fumes trapped by dilute sodium hydroxide. The reaction temperature rises to 92° C., and is then maintained at 100° C. for 1 hour. The solution is cooled by means of an ice bath and it is then made alkaline using sodium bicarbonate. The solution is filtered, the inorganic salts are washed three times with 300 ml of ethanol and the alcoholic filtrate is then evaporated. The solid residue is recrystallised from water. It is drained, washed with a minimum amount of water and then dried under vacuum. 22 g of compound are obtained.

Melting point: 185° C.

3.6. 4-(5-Methyl-1H-imidazol-4-yl)piperidine hydrochloride (2:1).

22 g (0.138 mole) of the above compound, 80 ml of concentrated hydrochloric acid, 500 ml of water and 3 g of charcoal containing 5% rhodium are introduced into a Parr apparatus. The mixture is stirred at 35° C. under a pressure of 0.35 MPa. After 4 hours, the hydrogenation is stopped; the catalyst is filtered and the filtrate is evaporated under vacuum. The residue is taken up in a mixture of ethanol and toluene. The resulting suspension is evaporated under vacuum to remove traces of water. The solid residue is taken up in 50 ml of hot ethanol. This solution is cooled, the precipitate is drained, washed with ethanol and dried under vacuum over phosphorus pentoxide. 26 g of compound are obtained.

Melting point: 320° C.

3.7. 2-[4-(5-Methyl-1H-imidazol-4-yl)piperidin-1-yl]-1(1-methylethyl)-1H-benzimidazole.

34 ml (0.18 mole) of 5.3 N sodium methylate are added, under argon, to a suspension of 21.5 g (0.0904 mole) of the above compound in 100 ml of methanol. The mixture is stirred for 15 minutes and then concentrated under vacuum to two thirds its volume. 200 ml of dichloromethane are then added and sodium chloride is filtered off. The solution is concentrated under vacuum and the crystallised base is recovered. A solution of 400 ml of 3-methylbutan-1-ol and 8.8 g (0.0452 mole) of 2-chloro-1-(1-methylethyl)-1H-benzimidazole are then added.

The mixture is heated at 120° C. by means of an oil bath for 24 hours. The precipitate of excess (6 g) piperidine hydrochloride (1:1) is filtered. The filtrate is evaporated to dryness and the residue is purified on a silica gel column eluting with a mixture of dichloromethane and methanol in proportions of 90:10 v/v. The pure fractions are combined and evaporated. The solid is washed with acetone and then dried under vacuum. 9.5 g of compound are obtained.

Melting point: 258° C.

EXAMPLE 4

2-[4-(1H-imidazol-4-yl)piperidin-1-yl]-1-(1-methylethyl)-1H-benzimidazole.

4.1. 1-(Pyridin-4-yl)ethanone-oxime.

A solution of 139 g (2 moles) of hydroxylamine hydrochloride in 280 ml of water is added, in a round bottomed flask, to a solution of 200 ml (2 moles) of 10 N sodium hydroxide in 180 ml of water while maintaining the temperature at around −5° C. 200 g (1.65 moles) of 1-(pyridin-4-yl)ethanone are rapidly added and the stirring is continued for 2 hours at 0° C. The precipitate formed is filtered and washed several times with ice-cold water. It is recrystallised from 4 liters of hot water and the solution is allowed to cool overnight. The crystals are drained, washed with water and dried in an oven over phosphorus pentoxide. 148 g of compound are obtained.

Melting point: 153° C.

4.2. 1-(Pyridin-4-yl)ethanone-o-[(4-methylphenyl)sulphonyl]oxime.

148 g (1.09 moles) of the above compound are added to a solution of 261 g (1.37 moles) of tosyl chloride in 550 ml of pyridine, cooled to 0° C. The reaction mixture is allowed to reequilibrate to room temperature and it is stirred for 48 hours. The solution is then poured onto 3 liters of ice-cold water, the precipitate formed is drained, washed with water and then dried under vacuum over phosphorus pentoxide. It is recrystallised from 600 ml of isopropyl alcohol, drained, washed with hexane and dried under vacuum. 275 g of compound are obtained.

Melting point: 80° C.

4.3. 2-Amino-1-(pyridin-4-yl)ethanone hydrochloride (2:1).

100 g (1.19 moles) of potassium ethylate powder are added, at 0° C. and under an argon atmosphere, to a 6-liter reactor containing 500 ml of absolute ethanol. A lukewarm solution of 295 g (1.017 moles) of the above compound in 1.5 liters of absolute ethanol is then added so that the reaction temperature does not exceed 0° C. The mixture is then allowed to reequilibrate to room temperature and it is again stirred for 1 hour. 4 liters of anhydrous ether are then added and the potassium tosylate precipitate is filtered. The organic filtrate is added slowly, and under an argon atmosphere, to a solution of 350 ml (2.1 moles) of 6 N hydrochloric acid in 800 ml of water. The mixture is decanted, the organic phase is washed again with 200 ml of 2 N hydrochloric acid, the aqueous phases are combined and concentrated under vacuum at a temperature of not more than 40° C. The crystallised residue is taken up in 200 ml of hot ethanol. The mixture is cooled, filtered, washed with ethanol and then the precipitate is dried under vacuum. 200 g of compound are obtained.

Melting point: 230° C.

4.4. 4-(2-Mercapto-1H-imidazol-4-yl)pyridine.

A mixture of 200 g (0.956 mole) of the above compound, 92.8 g (0.956 mole) of potassium thiocyanate and 800 ml of water is heated at 110° C. by means of an oil bath for 1.5 hours. The mixture is allowed to cool to around 40° C., the precipitate formed is filtered and washed with water. 80 g (0.95 mole) of sodium bicarbonate in 500 ml of water are then added in small portions. The precipitate is filtered, washed with water and dried under vacuum. 66.5 g of compound are obtained.

Melting point: >290° C.

4.5. 4-(1H-Imidazol-4-yl)pyridine.

66 g (0.372 mole) of the above compound in a solution of 550 ml of nitric acid (d = 1.41) and 3.2 liters of water are introduced into a 10-liter reactor. The mixture is heated to 90° C. while stirring thoroughly, and the reaction occurs violently with the release of sulphurous fumes which are trapped by dilute sodium hydroxide. and the reaction temperature rises to 95° C. and is then maintained at 100° C. for 1 hour. The mixture is then cooled to −7° C.: a filtrate is formed; it is drained and washed with a small amount of ice-cold water. The wet precipitate is then taken up in 130 ml of hot water. 72 g of sodium bicarbonate powder are then added in small portions, thereby causing crystallisation. The mixture is cooled by means of an ice bath, the crystals are drained and dried under vacuum; they are taken up several times in a hot solution of dichloromethane and methanol (90:10 v/v) so as to remove the inorganic salts. The filtrate is concentrated and 42.4 g of pure compound are obtained.

Melting point: 185° C.

4.6. 4-(1H-imidazol-4-yl)piperidine hydrochloride (2:1).

42 g (0.289 mole) of the above compound dissolved in 156 ml of concentrated hydrochloric acid and 900 ml of water, are introduced into a Parr apparatus, in the presence of 5% rhodium on carbon. The hydrogenation is carried out at 35° C. under a pressure of 0.35 MPa. After stirring for 4 hours, the reduction is discontinued. The catalyst is filtered and the filtrate is evaporated. The residue is taken up in a mixture of ethanol and toluene in proportions of 50:50 v/v. The resulting suspension is evaporated under vacuum to remove traces of water. The solid residue is then taken up in 100 ml of hot ethanol. The mixture is cooled, drained, washed with ethanol and then dried under vacuum over phosphorus pentoxide. 61 g of compound are obtained.

Melting point: 290° C.

4.7. 2-[4-(1H-imidazol-4-yl)piperidin-1-yl]-1-(1-methylethyl)-1H-benzimidazole.

47.3 ml (0.25 mole) of sodium methylate are added to a solution of 27.6 g (0.123 mole) of the above compound. The mixture is stirred for 15 minutes and it is, concentrated under vacuum to two thirds its volume, and 200 ml of dichloromethane are added. The sodium chloride precipitate which forms Is filtered. The filtrate is concentrated under vacuum. The crystallised residue is reacted with 12 g (0.061 mole) of 2-chloro-1-(1-methylethyl)-1H-benzimidazole in 60 ml of 3-riethybutan-1-ol at 120° C. for 36 hours. The precipitate of excess (8 g) piperidine monohydrochloride is filtered. The filtrate is evaporated to dryness. The residue obtained is purified on a silica gel column eluting with a mixture of dichloromethane and methanol in proportions ranging from 95:5 to 90:10 v/v. The pure fractions are combined and evaporated. The solid is washed with ether and dried under vacuum. 14.3 g of compound are obtained.

Melting point: 183° C.

The following table illustrates the chemical structures and the physical properties of some compounds according to the invention.

TABLE

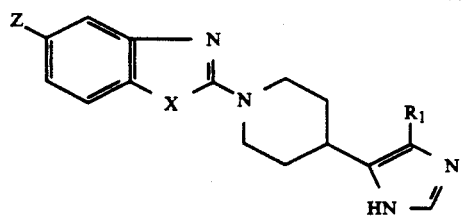

| No. | R₁ | X | Z | m.p. (°C.) | Salt |
|---|---|---|---|---|---|
| 1 | $CH_3$ | $N-CH(CH_3)_2$ | H | 258 | — |
|  |  |  |  | 182 | fum. (3:2) |
|  |  |  |  | 163-165 | mal. (1:2) |
| 2 | H | $N-CH(CH_3)_2$ | H | 183 | — |
| 3 | $CH_3$ | S | H | 190 | mal. |
| 4 | H | $N-C_6H_5$ | H | 202 | fum. (3:2) |
| 5 | H | $N-n-C_8H_{17}$ | H | 149-151 | fum. |
| 6 | H | $N-CH_3$ | H | 220-223 | — |
| 7 | H | $N-CH_2-cC_6H_{11}$ | H | 85-95 | — |
| 8 | H | $N-n-C_3H_7$ | H | 152-155 | fum. |
| 9 | H | $N-CH_2-CH(CH_3)_2$ | H | 118-123 | — |
| 10 | H | $N-CH_2-4-C_5H_4N$ | H | 238-243 | — |
| 11 | H | $N-CH_2-3-C_5H_4N$ | H | 243 | — |
| 12 | H | $N-(CH_2)_2-OCH_3$ | H | 168-173 | oxa. |
| 13 | H | $N-CH_2-cC_3H_5$ | H | 175-180 | fum. |
| 14 | H | $N-CH(CH_3)_2$ | F | 185 | — |
| 15 | $CH_3$ | $N-C_6H_5$ | H | 142-145 | fum. (3:2) |
| 16 | $CH_3$ | $N-CH_2-cC_3H_5$ | H | 85-90 | — |
| 17 | $CH_3$ | $N-n-C_3H_7$ | H | 177 | mal. (2:1) |
| 18 | $CH_3$ | $N-CH_2-CH(CH_3)_2$ | H | 214-215 | oxa. |
| 19 | $CH_3$ | $N-CH_2-cC_6H_{11}$ | H | 90-98 | — |
| 20 | $CH_3$ | $N-n-C_8H_{17}$ | H | 121-123 | fum. (5:2) |
| 21 | $CH_3$ | $N-CH_2-3-C_5H_4N$ | H | 196 | — |
| 22 | $CH_3$ | $N-(CH_2)_2-OCH_3$ | H | 187-190 | oxa. |
| 23 | $CH_3$ | NH | H | >270 | h. chlor. (2:1) |
| 24 | $CH_3$ | $N-CH(CH_3)_2$ | F | 270-275 | — |
| 25 | $CH_3$ | $N-CH_3$ | H | 248-250 | oxa. (1:2) |
| 26 | H | S | H | 174 | mal. |
| 27 | $CH_3$ | $N-CH_2-4-C_5H_4N$ | H | 96-104 | — |
| 28 | H | O | H | 182-186 | — |
| 29 | H | NH | H | >230 | — |
| 30 | $CH_3$ | $N-cC_3H_5$ | H | 185-195 | fum. |
| 31 | H | $N-cC_3H_5$ | H | 205-210 | — |
| 32 | $C_2H_5$ | $N-CH(CH_3)_2$ | H | >210 | — |
| 33 | $CH(CH_3)_2$ | $N-CH(CH_3)_2$ | H | 108-115 (d) | — |
| 34 | $cC_6H_{11}$ | $N-CH(CH_3)_2$ | H | 130-135 (d) | — |

NB: in the column "X" of the table
$cC_6H_{11}$ denotes cyclohexyl,
$4-C_5H_4N$ denotes pyridin-4-yl,
$3-C_5H_4N$ denotes pyridin-3-yl,
$cC_3H_5$ denotes cyclopropyl;
in the column "m.p. (°C.)" of the table
(d) denotes decomposition
in the column "salt" of the table
(x:y) denotes x moles of acid per y moles of base, the absence of any comment means that the compound is in the form of a base,
h. chlor. represents hydrochloride,
fum. represents fumarate,
mal. represents maleate,
oxa. represents oxalate.

The compounds of the invention have been the subject of pharmacological trials which have shown their usefulness as therapeutically active substances.

Thus, they have been tested with respect to their inhibitory effects on the binding of [³H]quipazine to 5-HT₃-type serotoninergic receptors which are present in the cerebral cortex of rate, according to a variant of the method described by Milburn and Peroutka (J. Neurochem., 52, 1787-1792, 1989). 150 to 200-g male Sprague-Dawley rats are used in all the trials. Their cerebral cortex is removed and homogenised in 20 volumes (weight/volume) of 25 mM Hepes buffer or 25 mM Herpes buffer containing sodium chloride (180 mM), calcium chloride (2.5 mM), potassium chloride (5 mill) and magnesium chloride (1.2 mM) (pH=7.4), by means of a Polytron TM grinder. After centrifuging the suspension for 10 min at 45,000 x g, the pellet is resuspended in the initial volume of buffer optionally containing 0.05% of Triton X-100 TM, and a first incubation is carried out for 30 min at 37° C. Two additional centrifugations are then carried out as described above and the final pellet is taken up in 11.7 volumes of 25 mM Hepes buffer at pH=7.4. The [³H]quipazine binding is measured (51.6–69.8 Ci/mmol, New England Nuclear, Boston, Mass., USA) by incubating 150 μl of the membranous suspension with the radioligand (0.8 nM) in a final volume of 1 ml for 30 min at 25° C. in the absence or in the presence of the test compound. The incubation is performed in the presence of 0.1 μM of paroxetine and 1 μM of ketanserin. Nonspecific binding is measured in the presence of 1 μM of ondansetron. After incubation, the test mixture is diluted with 5 ml of 50 mM ice-cold Tris-HCl buffer (pH=7.4 at 0°C.). The membranes are recovered by filtration on Whatman GF/B TM filters pretreated with 0.05% of polyethylenimine, and they are washed with three volumes of 5 ml of 50 mM ice-Cold Tris-HCl buffer.

The radioactivity retained on the filters is measured by liquid scintillation spectrometry at an efficiency of 50 to 60%.

The results are expressed as the concentration (IC₅₀) of the test compound which inhibits 50% of the [³H]quipazine binding, determined by a graphical or mathematical method. The compounds of the invention which are most active in this trial are characterised by IC₅₀ values of less than 1 nM ($10^{-9}$M).

The compounds of the invention were also tested with respect to their effect on the Bezold-Jarisch reflex, that is to say an intense bradycardia caused by intravenous injection of serotonin. This reflex calls into play the stimulation of 5-HT₃-specific receptors of the vagus nerve, which causes a depolarisation and therefore a secretion of acetylcholine which is the natural vagal neurotransmitter. Male Sprague-Dawley rats are anaesthetised with urethane (1 to 25 g/kg via intraperitoneal administration), the blood pressure is measured by means of a catheter placed in the carotid artery, and pressure pulses are used to activate a cardiotachometer. Cannulas are inserted in the two femoral veins in order to facilitate the intravenous administration of the products. Dose/response curves are plotted for the bradycardia caused by the injection of doses of 30 μg/kg of serotonin before and after injection of the test compounds. The compounds of the invention which are most active in this trial inhibit the serotonin-induced bradycardia by at least 50% at an intravenously administered dose of 10 μg/kg.

Another in vivo test is that of the emptying of the stomach in rats, according to a procedure described by Scarpignato (J. Pharmacol., (Paris) 14(2). 261-268, 1983). The animals are 180 to 200-g male CD rats that have been starved for 24 h. The test compounds are administered intraperitoneally or orally 15 or 30 min before absorbing an indigestable liquid meal (methylcellulose and phenol red). The animals are sacrificed 10 min after administering the meal and the amount of phenol red remaining in the stomach is assayed by spectrophotometry, a group of control rats being sacrificed immediately after the meal.

The compounds of the invention which are most active in this trial increase the emptying of the stomach after an intraperitoneally or orally administered dose of 1 mg/kg.

The compounds of the invention were also studied with respect to their effects on emesis in ferrets (male, 1 to 1.4 kg), according to a method described by Costall et al., (Neuropharmacology 25(8), 959-961, 1986). The test compounds or saline are administered intravenously (jugular vein), under halothane anaesthesia, immediately before an intravenous infusion of cisplatin (10 mg/kg in 10 min). The animals are then observed for 3 h, noting the number of emetic episodes, the total number of spasms and vomiting as well as the time taken before the appearance of the first attack. The compounds of the invention which are most active in this trial show an antiemetic effect after intravenous administration of a dose of less than 5 mg/kg.

Finally, the compounds of the invention were studied with respect to their effects on the atypical 5-HT receptors (5-HT$_4$) in the ileum of guinea pigs, according to Craig and Clarke, J. Pharm. Exp. Ther., 252 (3), 1378-1386, (1990). 300 to 400-g male Jegard three-colored guinea pigs are killed and bled. A fragment of the ileum of about 3 cm is rapidly removed in the region of the ileocaecal junction and it is washed with 10 ml of lukewarm Krebs buffer (composition in mM: NaCl=118; CaCl$_2$ =2.6; KCl=4.9; NaH$_2$PO$_4$=1; MgSO$_4$=1.2; NaHCO$_3$=25; glucose =11.7). The ileum is mounted on a 2-ml pipette and the longitudinal muscle is carefully separated with dental cotton wool impregnated with Krebs buffer. The organ is connected to an isometric transducer at a basal tension of 0.5 g and maintained in a Krebs bath at 37° C. which is aerated with a carbogen stream. After a rest time of about 30 min, an electric stimulation is applied (0.2 Hz; 1.5 ms; supramaximal voltage ≦45 V) by means of H. Sachs model F2H field electrodes linked to a Grass S88 TM stimulator until the contractions (or "twitches") are stabilised. 3×10$^{-7}$ phenoxybenzamine is then added to the bath, which reduces the amplitude of the contractions up to about 50% (≦30 min). The organ is then washed six times at 5 min intervals. Serotonin (3×10$-7$ M) is added before the fourth wash. If necessary, the amplitude of the contractions is reduced to 50% of the supramaximal amplitude by reducing the electric voltage after the sixth wash. A graph of concentration effect by cumulative additions, at 1 min intervals, of the test compound is plotted. The responses are measured in terms of the capacity to restore the amplitude of the contractions to the level of that obtained by means of the supra-maximal voltage and after treatment with phenoxybenzamine. The compounds of the invention behave like agonists, partial agonists or antagonists of the said receptors, some of them being active at concentrations of less than 10 nM.

The results of the biological tests show that the compounds of the invention are serotoninergic receptor ligands. As shown above, they interact in particular with the 5-HT$_3$ and 5-HT$_4$-type receptors. They can therefore be used in the treatment and prevention of disorders in which 5-HT receptors are involved, such as nausea and vomiting, for example resulting from an antitumour treatment or from the administration of an anaesthetic; disorders of the central nervous system such as schizophrenia; mania, anxiety and depression; cognition disorders such as Alzheimer's senile or presenile dementia; dyskinesia, pain, migraine and headaches; disorders resulting from dependency on or withdrawal from alcohol or drugs; disorders of the gastrointestinal function such as dyspepsia, peptic ulcer, pyrosis, flatulence; disorders of the cardiovascular system and respiratory disorders.

For that purpose, they may be provided in any form suitable for oral or parenteral administration, such as tablets, sugared pills, hard gelatin capsules, capsules, suspensions or solutions taken orally or injected and the like, in combination with appropriate excipients, and in doses which permit administration of 0.005 to 5 mg/kg, 1 to 4 times daily.

Appendix

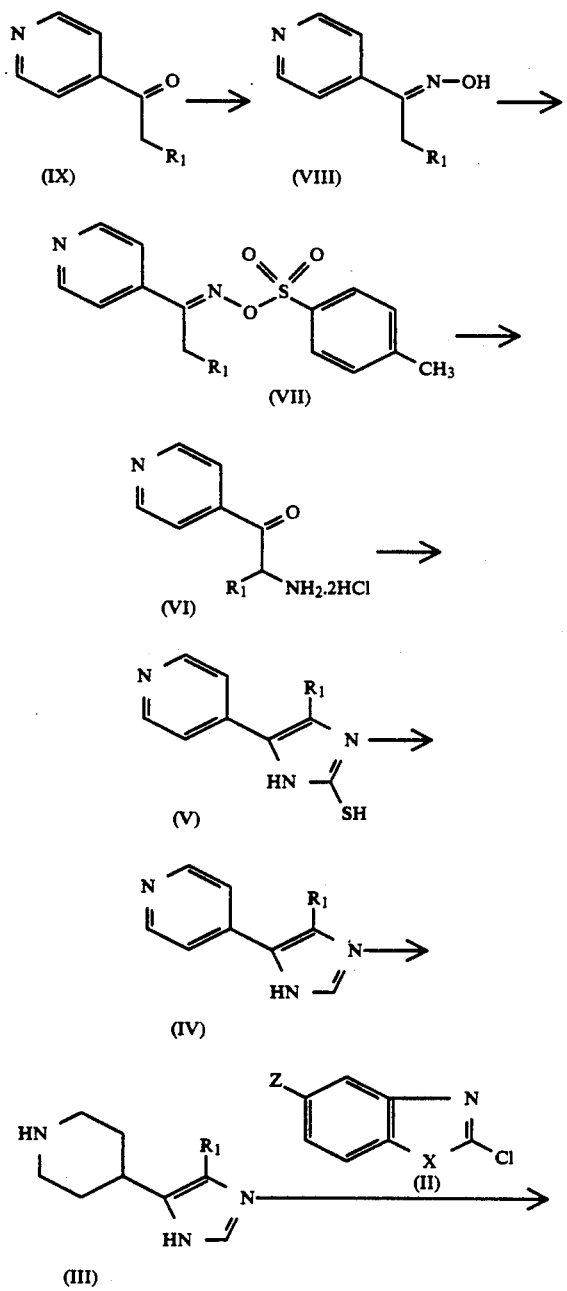

-continued

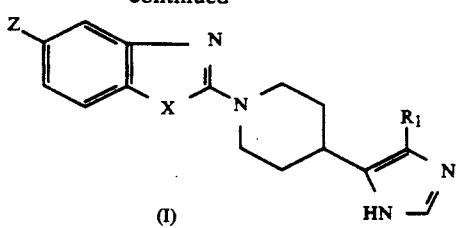

(I)

We claim:
1. A compound of formula (I)

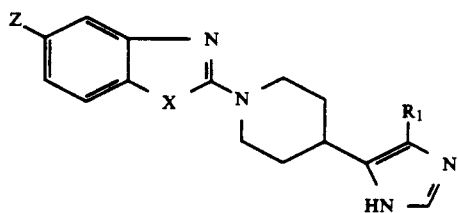

(I)

in which $R_1$ represents a hydrogen atom, a linear or branched $(C_{1-6})$alkyl group or a cyclo$(C_{3-8})$alkyl group, X represents an oxygen atom, a sulphur atom or N—$R_3$ in which $R_3$ is a hydrogen atom, or a linear or branched $(C_{1-8})$alkyl, cyclo$(C_{3-6})$alkyl, cyclo$(C_{3-6})$alkylmethyl, $(C_{1-4})$alkoxy-$(C_{1-4})$alkyl, phenyl, pyridin-4-yl, pyridin-3-yl, pyridin-4-ylmethyl or pyridin-3-ylmethyl group and Z represents a hydrogen or fluorine atom or an acid addition salt thereof with a pharamaceutically acceptable acid.

2. A compound according to claim 1 in which $R_1$ represents a hydrogen atom or a methyl or cyclohexyl group, X represents an oxygen atom, a sulphur atom or N—$R_3$ in which $R_3$ is a hydrogen atom, or a linear or branched $(C_{1-8})$alkyl, cyclopropyl, cyclo$(C_{3-6})$alkylmethyl, methoxyethyl, phenyl, pyridin-4-ylmethyl or pyridin-3-ylmethyl group and Z represents a hydrogen or fluorine atom.

3. A compound according to claim 1, in which $R_1$ represents a hydrogen atom or a linear or branched $(C_{1-6})$ alkyl group, X represents N—$R_3$ in which $R_3$ is a linear or branched $(C_{1-8})$alkyl group and Z represents a hydrogen atom.

4. 2-[4-(5-Methyl-1H-imidazol-4-yl)piperdin-1-yl ]-1-(1-methylethyl)-1H-benzimidazole or an acid addition salt thereof with a pharmaceutically acceptable acid.

5. 2-[4-(1H-Imidazol-4-yl)piperidin-1-yl]-1-methylethyl)-1H-benimidazole or an acid addition salt thereof with a pharmaceutically acceptable acid.

6. A compound according to claim 1 in which the acid addition salt is the hydrochloride, fumarate, maleate or oxalate.

7. A pharmaceutical composition comprising, as active ingredient a compound as claimed in claim 1, together with a pharmaceutically acceptable excipient.

* * * * *